US008412542B2

(12) United States Patent
Mok et al.

(10) Patent No.: US 8,412,542 B2
(45) Date of Patent: Apr. 2, 2013

(54) SCORING SYSTEM FOR MONITORING OR MEASURING ADHERENCE IN MEDICAL TREATMENT

(75) Inventors: Megan Mok, Pacifica, CA (US); Haya Rubin, Palo Alto, CA (US); Whitney Limm, Honolulu, HI (US)

(73) Assignee: PeopleChart Corporation, San Francisco, CA (US)

( * ) Notice: Subject to any disclaimer, the term of this patent is extended or adjusted under 35 U.S.C. 154(b) by 397 days.

(21) Appl. No.: 12/233,440

(22) Filed: Sep. 18, 2008

(65) Prior Publication Data

US 2009/0271218 A1    Oct. 29, 2009

Related U.S. Application Data

(60) Provisional application No. 61/048,103, filed on Apr. 25, 2008.

(51) Int. Cl.
*G06F 17/60* (2006.01)
*G06F 19/00* (2011.01)

(52) U.S. Cl. ................................. 705/3; 705/2
(58) Field of Classification Search ........................ 705/3
See application file for complete search history.

(56) References Cited

U.S. PATENT DOCUMENTS

| | | | |
|---|---|---|---|
| 6,802,810 B2 | 10/2004 | Ciarniello | |
| 6,820,085 B2 | 11/2004 | Nishizawa | |
| 7,039,628 B2 | 5/2006 | Logan | |
| 7,234,064 B2 * | 6/2007 | Menschik et al. ............ 713/193 |
| 2002/0010597 A1 | 1/2002 | Mayer | |
| 2002/0029157 A1 | 3/2002 | Marchosky | |
| 2002/0120472 A1 | 8/2002 | Dvorak | |
| 2002/0147611 A1 | 10/2002 | Greene | |
| 2002/0194022 A1 | 12/2002 | Comite | |
| 2003/0088440 A1 | 5/2003 | Dunn | |
| 2003/0115084 A1 | 6/2003 | Gage | |
| 2003/0125985 A1 * | 7/2003 | Rao et al. ............ 705/2 |
| 2003/0140044 A1 | 7/2003 | Mok | |
| 2003/0208381 A1 | 11/2003 | Walter et al. | |
| 2004/0044546 A1 | 3/2004 | Moore | |
| 2004/0117215 A1 | 6/2004 | Marchosky | |
| 2004/0186746 A1 | 9/2004 | Angst | |
| 2004/0210458 A1 | 10/2004 | Evans | |
| 2005/0086074 A1 | 4/2005 | Punzak | |
| 2005/0086082 A1 | 4/2005 | Braunstein | |
| 2005/0119917 A1 | 6/2005 | Kim | |
| 2005/0216313 A1 | 9/2005 | Claud | |
| 2006/0004609 A1 * | 1/2006 | Kenneth et al. ............ 705/3 |
| 2006/0041452 A1 | 2/2006 | Kulkarni | |
| 2006/0173712 A1 | 8/2006 | Joubert | |
| 2007/0027720 A1 | 2/2007 | Hasan | |
| 2007/0027722 A1 | 2/2007 | Hasan | |
| 2007/0050214 A1 * | 3/2007 | Hawks et al. ............ 705/3 |
| 2007/0055552 A1 | 3/2007 | St. Clair | |

(Continued)

*Primary Examiner* — Hiep V Nguyen
(74) *Attorney, Agent, or Firm* — Brian N. Young; Fountainhead Law Group P.C.

(57) ABSTRACT

Particular embodiments provide a quality adherence guide. In one embodiment, a plurality of medical records from a plurality of medical providers are received. A quality adherence guideline is used to determine if a standard of care is being adhered to by various medical providers. A quality adherence guideline is then generated using the selected standard of care. The quality adherence guideline includes a set of treatment steps that are defined by the selected standard of care. Information from the medical records associated with the patient is also used to populate the guide. During treatment of the patient, input may be received from a plurality of users from health care providers regarding the treatment steps. The patient-direct system automatically analyzes the information inserted in the guideline to determine the level of adherence that various users have achieved when compared with the industry standard for quality care.

20 Claims, 9 Drawing Sheets

U.S. PATENT DOCUMENTS

| | | |
|---|---|---|
| 2007/0078686 A1 | 4/2007 | Dettinger |
| 2007/0078687 A1 | 4/2007 | Dettinger |
| 2007/0150315 A1 | 6/2007 | Bennett |
| 2007/0167687 A1 | 7/2007 | Bertolero |
| 2007/0192137 A1 | 8/2007 | Ombrellaro |
| 2007/0198296 A1 | 8/2007 | Pellinat |
| 2007/0203754 A1 | 8/2007 | Harrington |
| 2008/0033751 A1 | 2/2008 | Greene |
| 2008/0052111 A1 | 2/2008 | McMenimen |
| 2008/0059242 A1 | 3/2008 | Stanford |

* cited by examiner

| Quality Milestone Indicator 902 | Yes/No Response 904 | Target Date 906 | Recommended Role (User Type) To Provide Answer 908 | Recommended Action Step (For Quality Milestone) 910 | Information Adequacy Score 912 |
|---|---|---|---|---|---|
| Does patient have breast cancer stage I to IIIA? | Yes / No System generates alert to patient! | NA | Breast surgeon; Oncologist; patient Please input their names and contact information here for tracking and communications. | You have not answered or received answer from your physician for this step! If you do not know answer, please check with: √ (yes) oncologist; X (no) breast surgeon; | Your information adequacy score is 45%. Click here for pop-up table for details and recommendations. |
| | | | | √ Initiate e-notification to be sent to (please select): x Breast Surgeon; √ Oncologist, etc. | |

*Fig. 8*

| Quality Milestone Indicator | Target Information Needed | Information Adequacy (Score) | Source of Information | Recommended Action Step (For Information Adequacy) |
|---|---|---|---|---|
| Does patient have breast cancer stage I to IIIA? | You need to have the following information:<br><br>☑Biopsy results (5=Highly Important; Must Have) Date Received:<br><br><u>System generates alert to patient</u><br><br>☒Cancer Marker Test A (2=Somewhat Important) Date Received:<br><br>☒Oncology report (3=Important) Date Received:<br><br>☒ Cancer Marker Test B (4=Very Important) Date Received: | When all information requirements are met, you receive a score of 100%.<br><br>So far, your Information Adequacy Score is 45%.<br><br>This is below the level of adequate information needed by your physicians to make a good decision.<br><br><u>System generates alert to patient!</u> | Gynecologist; Primary; Oncologist, etc. | √<u>Upload file (if you have information by clicking here)</u>.<br><br>√<u>Initiate medical record collection by clicking here</u>.<br><br>√<u>Initiate e-notification to be sent to (please select):</u> __Gynecologist; __Primary; __Oncologist, etc. |

*Fig. 9*

SCORING SYSTEM FOR MONITORING OR MEASURING ADHERENCE IN MEDICAL TREATMENT

CROSS REFERENCES TO RELATED APPLICATIONS

This application claims priority from U.S. Provisional Patent Application Ser. No. 61/048,103 entitled "Monitoring Quality of Treatment Decisions and Information Adequacy Using Patient-Directed System (PHR)", filed on Apr. 25, 2008, which is hereby incorporated by reference as if set forth in full in this application for all purposes.

BACKGROUND

Particular embodiments generally relate to medical records management systems.

Some single provider systems allow their patients to access information about their test results and medications ordered. A patient can then access his/her medical records via a web portal associated with the health care provider. However, the system is tethered to the single provider and does not allow the patient to save and download personal health information from the web portal. Basically, the information is accessible to the patient only for as long as the patient is affiliated with the health care organization.

Personal health records allow users to access and coordinate their lifelong health information. This allows a user to aggregate medical information from multiple providers, such as different physicians, health care facilities, insurers, and other entities. Previously, a user's health records were separately maintained by single providers, such as a single medical group. However, a robust personal health record system is able to allow a user's medical information to be consolidated from multiple providers and to be portable with the user even when the user terminates care from the health care provider.

As patient care becomes more complicated, users sometimes seek treatment from different health care providers. The personal health record system allows aggregation of health records but sometimes the aggregation of records may be confusing or hard to understand when they are aggregated from multiple health care providers. This makes it harder for a user to determine if the quality of care being administered by the multiple health care providers is adequate or not. Also, the single provider systems are specific to each different provider and thus the user is forced to use the single provider's preferred standard of care.

SUMMARY

Particular embodiments generally relate to medical records management systems and more specifically to a system for providing quality adherence for a patient using a quality adherence guide. In one embodiment, a plurality of medical records from a plurality of medical providers are received. A patient can authorize release of the plurality of medical records from the plurality of medical providers, where the plurality of medical records can be aggregated into a personal health record. The personal health record system is controlled by the patient.

A quality adherence guideline is used to determine if a standard of care is being adhered to by various medical providers. The system may output a plurality of standards of care that may be used. The standards of care relate to a medical condition associated with the patient. The different standards of care may detail a number of treatment recommendations that are supported by different industry groups in treating the medical condition. An input can then be received from the patient selecting a standard of care.

A quality adherence guideline is then generated using the selected standard of care. The quality adherence guideline includes a set of treatment steps that are defined by the selected standard of care. Information from the medical records associated with the patient is also used to populate the guide. For example, relevant information for the treatment recommendations from the plurality of medical records may be automatically populated/displayed or manually self-entered into the guide.

During treatment of the patient, input may be received from a plurality of users from two or more of the plurality of health care providers regarding one or more of the treatment steps. The input is related to the patient's treatment with regard to the one or more treatment steps. The patient selects from the plurality of user(s) and identifies the user who enters the specific data required by the guide, who receives the alerts for the guide, and who can complete the information in the guide or keep the guide updated with the most current information. The health care providers are assigned roles (user types) by the patient and the roles can represent the various disease specialties of the physicians or the functional title of the health professionals who are involved in the care of the patient. For certain questions in the guide, the designated user-respondent can include more than one person or role and can include the patient. The patient monitors the response and audits each step taken within the context of the protocols or recommendations generated by the guideline. When the healthcare provider is not available to answer the question, the patient can take on the back-up role and self-enter any known answer into the guide. When certain information or treatment steps are still missing or delayed, the patient can also authorize that notifications be sent to specific user(s) and/or any other recipient as desired by the patient. In this patient-directed system of healthcare quality improvement, the patient is both an active participant and auditor of health care quality.

The patient-direct system automatically analyzes the information inserted in the guideline to determine the level of adherence that various users have achieved when compared with the industry standard for quality care. For example, the quality adherence guideline is used to determine whether the appropriate treatment has been performed at the appropriate time. An alert may be outputted based on the analysis. For example, the alert may notify the patient that a treatment step has been missed, is forthcoming, or should be taken promptly. The quality adherence guideline thus allows the patient to participate, validate, and oversee the processes along which multiple healthcare providers must follow in order to satisfy certain minimally-accepted standard for quality care.

Also, a quality adherence score may be generated that measures or clearly indicates to the patient and other users of the guide whether and when certain milestones or standard-of-care guidelines are being met. The score determines how closely the user(s) are adhering to the protocols of care based on the information manually inputted or automatically populated into the guideline. In addition, an information adequacy score may be generated that measures or clearly indicates to the patient and other users of the guide whether existing clinical information stored in the core personal health record system that is displayed in the guide provide enough information upon which decisions are made about the next treatment step. Certain documents from the medical record repository and self-entered information stored in the core personal health records are compiled and displayed in the guide so that the patient and users of the guideline can view the patient-specific information within the context of the next treatment steps or guideline protocols. The adequacy of the information base help measure the relevancy and validity of the recommended steps based on the specific health history and profile of the patient.

A further understanding of the nature and the advantages of particular embodiments disclosed herein may be realized by reference of the remaining portions of the specification and the attached drawings.

DETAILED DESCRIPTION OF EMBODIMENTS

System Overview

Figure 1:
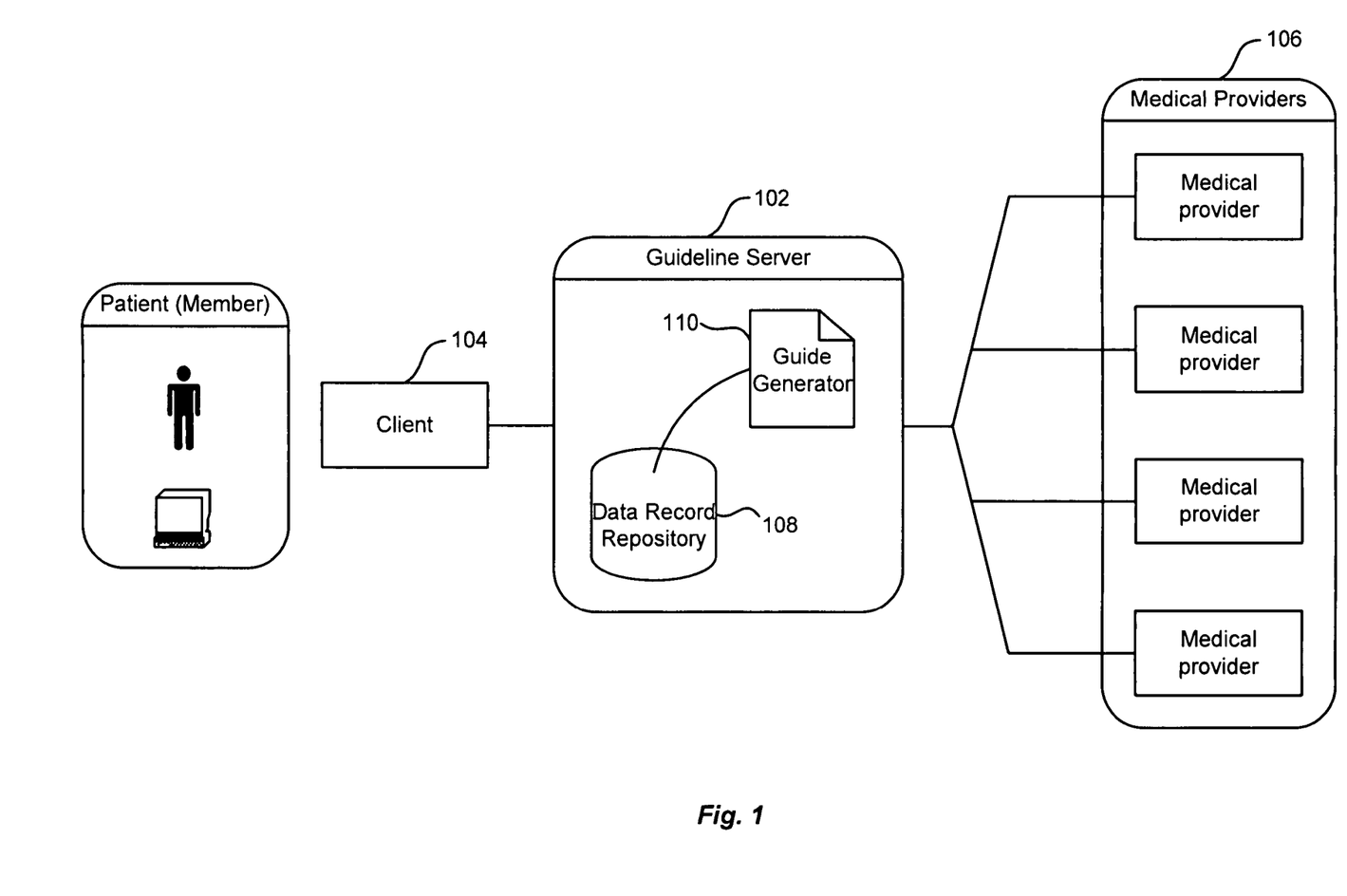
FIG. 1 depicts a health care quality improvement system according to one embodiment.

FIG. 1 depicts a health care quality improvement system 100 according to one embodiment. System 100 includes a guideline server 102, a client 104, and a plurality of medical providers 106.

Particular embodiments provide quality of care monitoring and alert generation methods in the context of a personal health record system (PHR) that is controlled by a patient. A set of guidelines are available for the patient to choose in order to ensure that the patient and health professionals can understand and maintain a certain level of quality care and complete certain treatment steps as specified in the guidelines. The guidelines may be generated based on industry-approved standards of care and industry-defined treatment steps. The patient selects from the plurality of user(s) and identifies the user who enters the specific data required by the guide, who receives the alerts, and who can complete the information or keep the guide updated with the most current information. The patient can monitor and audit each step taken by medical providers 106 within the context of the guideline. When certain information or treatment steps are missing or delayed, the patient can authorize notifications be sent to any user (as determined by the role type) and to any other recipient as desired by the patient. Thus, the patient is both an active participant and an auditor of the guideline.

Client 104 may be any computing system that can be used to interact with guideline server 102. For example, client 104 includes a personal computer, laptop computer, cellular phone, smart phone, or any other computing device. A patient may use a user interface on client 104 to interact with guideline server 102. The user interface may display a quality adherence guideline that allows steps to be taken by the patient as will be described below.

Medical providers 106 may be entities that provide health care or other related services to the patient. Medical providers 106 may include separate entities or groups that may not have a business relationship. For example, the medical providers may include one person (e.g., a sole practitioner), a group of persons (e.g., a family clinic), an organization (e.g., hospital or medical university), or other networks of doctors or service providers. A single medical providers 106 may be an owner or custodian of medical records for the patient. For example, an organization may own the medical records for a patient that receives treatment from the organization. Different medical providers 106 may be owners of their own record-keeping about the patient. Medical providers 106 may include a community of PHR users, including physicians, caregivers, designated agents, limited agents, family members, relatives, or other healthcare professionals. The PHR users are qualified to input information into the guideline for certain treatment steps.

A personal health record database may be provided for the patient. This stores medical records from the plurality of medical providers 106 in a data record PHR repository 108. This allows the stored information to be comprehensive and portable under the jurisdiction of the patient. A database designed around the patient provides the patient with the freedom and ability to choose with whom to share what type of information—a fundamental choice that defines ownership of the information by the patient. The personal health record is different from a provider-controlled medical record system in which each medical provider controls their own records. Accordingly, medical providers 106 may provide medical records to guideline server 102. The records can then be stored in a patient's personal health record in a database or medical record PHR repository 108. This provides access to a lifetime of health information about the patient that is complete and also portable. For example, as a patient visits different medical providers 106 or moves from one medical provider 106 to another medical provider 106, the medical records may follow the user as they have been stored in the patient's personal health record.

The personal health record may be any records that are personal to the patient. The PHR may be stored automatically based on rules for generating a PHR. Also, the system can have its own database to capture patient's medical records and other health information. For example, the patient can populate the guide with relevant data by (1) self-collect and upload the scanned documents to the decision support tool via browser-based internet connection; (2) self-enter the information into various health profile forms; and (3) request for electronic data transmittal via a service provider.

A guideline generator 110 is configured to generate the quality adherence guideline using information from a patient's personal health record. This provides a quality adherence guideline that is personalized for the patient and allows the patient to monitor the quality of care that is being provided by multiple medical providers 106. The guideline may be maintained by a company that is independent from medical providers 106 or an insurance company providing insurance to the patient. Thus, the guideline generator is free from any standards or influences that may occur if the guideline was maintained or associated with medical providers providing care for the patient or insurance companies providing insurance for care.

The quality adherence guideline determines if information from medical providers 106 adheres to a standard of care. It measures the type of information contributed by various medical providers 106 and whether there is enough information for other medical providers (or physicians) to make quality decisions. The guideline also monitors, validates, and oversees the adherence by physicians and other medical providers to the recommended standards of care as specified in the guideline.

Guideline server 102 may analyze information entered into it and generate alerts to both patients and patient-authorized physicians about the missing information that is needed and any delay in timing for information to be received. For example, the alerts may notify both patients and patient-authorized physicians when certain treatment steps may have been overlooked. Also, next steps in the treatment process may be suggested based on the standard of care specified in the guideline.

The guideline may also be analyzed to generate rating scores that allow a user to quickly determine the level of care received when compared with the standard. The rating scores include a quality adherence score and an information adequacy score. The quality adherence score and the information adequacy score may be generated based on the information manually-inputted or automatically populated into the guideline. The quality adherence score measures or clearly indicates to the patient and other users of the guide whether certain milestones or protocols-of-care are being met. It provides a quick way for measuring how closely the recommended protocols or standards are being followed by the various users during the course of treatment. The information adequacy score measures or clearly indicates to the patient and other user(s) of the guide whether existing medical records and clinical information stored in the core personal health record system provide an adequate base of information from which to make informed decisions about the next treatment step. The information adequacy score is a quick way to determine if there is enough information to go the next treatment step.

The guideline may require that a patient and PHR users for multiple medical providers 106 enter information into the guideline. Allowing both patient and PHR users to enter information in addition to the population of medical records retrieved from medical providers 106 stored in the PHR repository 108 enables a comprehensive set of information from which to analyze and determine if a standard of care is being met. PHR users and patients may be alerted to complete or respond to certain parts of the guide. This makes it more likely that information will be reviewed, taken seriously, and completed to the extent that it requires input by the patient and/or PHR users.

More Detailed Example of Guide Generator 102

Figure 2:
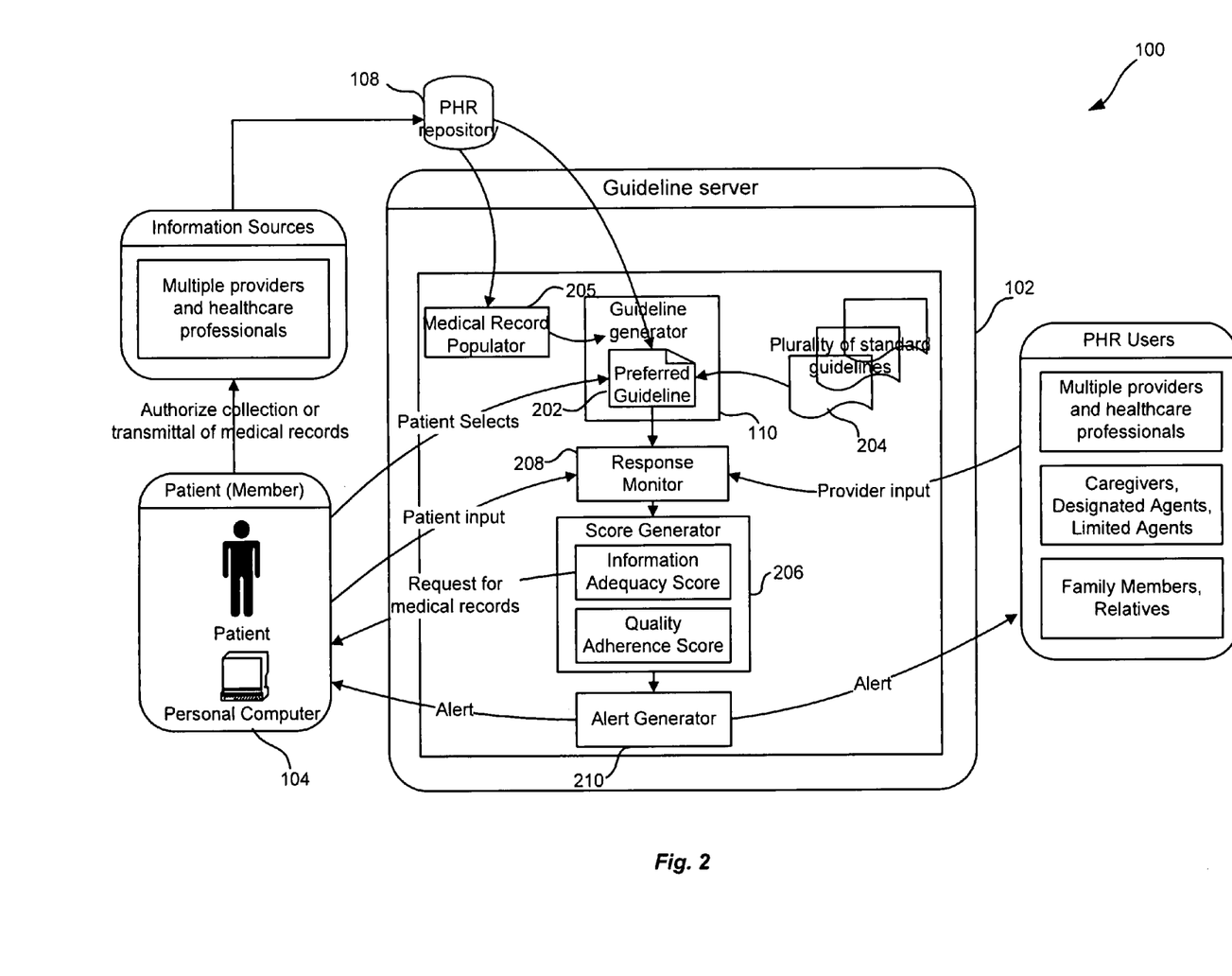
FIG. 2 depicts a more detailed example of healthcare quality improvement system according to one embodiment.

FIG. 2 depicts a more detailed example of healthcare quality improvement system 100 according to one embodiment. Guideline generator 110 is configured to generate a preferred guideline 202 from a plurality of standard guidelines 204. A patient may select preferred guideline 202 from the plurality of standard guidelines 204. The plurality of standard guidelines 204 may be based on industry-approved standard of care guidelines. For example, the industry-approved standard of care guidelines may be guidelines that are provided by universities, research organizations, or other entities. The standard of care guidelines may be selected by a patient, which is different from having medical providers 106 select which guideline is used for the treatment of the patient. For example, each medical provider 106 may have their preferred guidelines. However, the patient does not have input to determine how treatment is performed by medical provider 106. However, particular embodiments output a plurality of standard of care guidelines 204 to client 104. A user can then select a preferred guideline 202. Also, combinations of variations of standard of care guidelines 204 may be specified. For example, a first part of one guideline and a second part of a second guideline may be combined to form preferred guideline 202. Accordingly, a patient directs which quality of care guideline is used and how treatment is performed.

Quality of care guideline 204 may provide a plurality of treatment steps. The treatment steps are recommended medical solutions that are developed in response to certain diagnosis or condition that result in the course of treatment. For example, for a medical condition, such as cancer, a guideline will specify that certain steps need to be taken to treat the condition. Preferred guideline 202 recites these steps in a guideline form.

Figure 8:
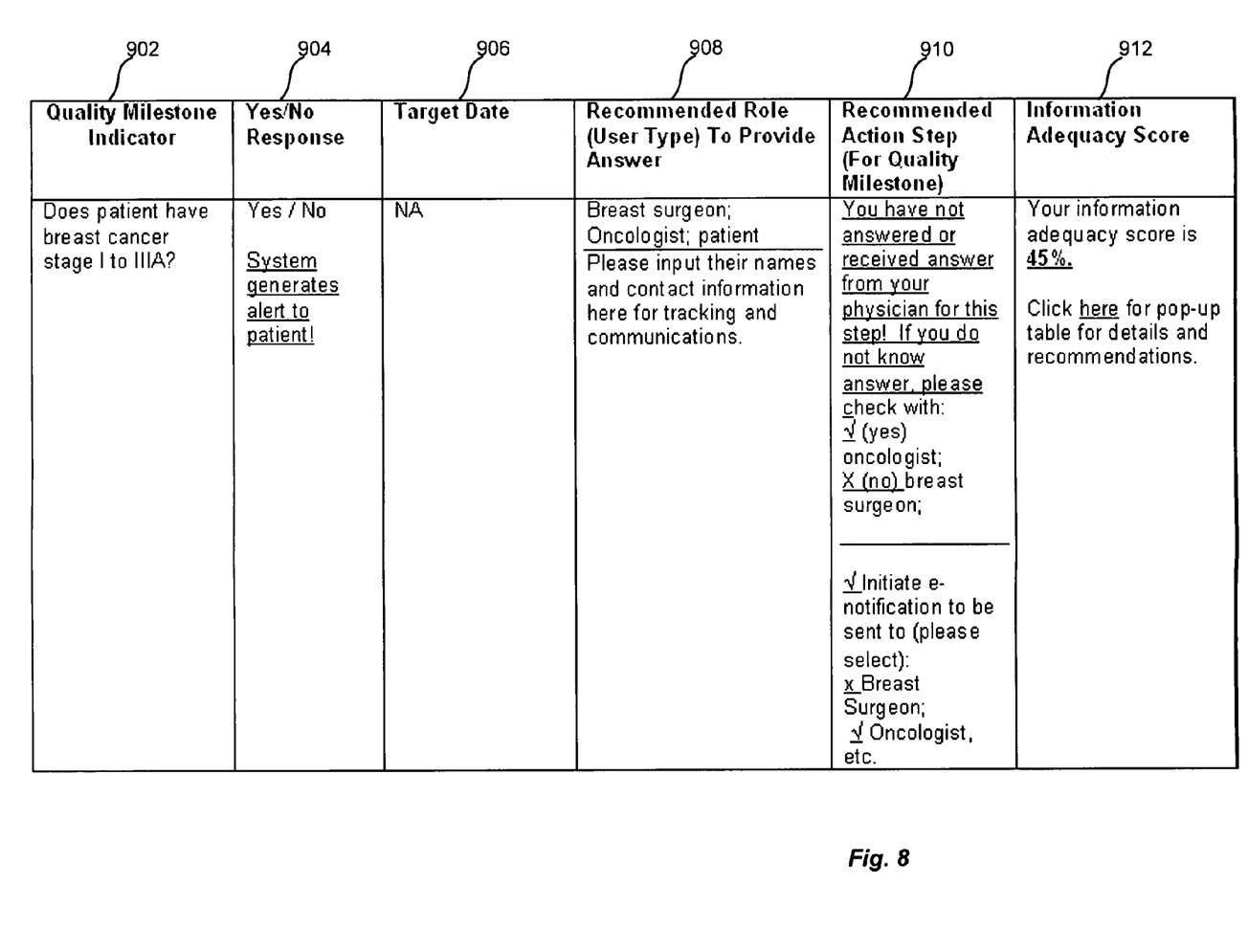
FIG. 8 shows an example of a guideline.

Referring to FIG. 8, an example of a guideline 202 is shown. Column 902 lists quality treatment steps. These are milestones that should be met for quality adherence to the standard of care. This column lists procedures or decision steps for treating a disease or preventing the occurrence of a disease or condition. The procedures or decisions steps follow the standard of care that has been selected by the patient.

Once the patient selects preferred guideline 202, it may be personalized with information associated with the patient. For example, the patient may have authorized collection of medical records from medical providers 106. The medical records may have been stored in data record PHR repository 108 in a personal health record. The information may be received in various forms. For example, information may include handwritten notes, text or word processing files, image files, films, video or audio clips, multimedia files, soft or hard copies of medical records, or other records. These records may be categorized and classified using automated methods or users may review the records and classify each record themselves by selecting the category from a list of categories presented in a patient's personal health record. Examples of methods that may be used to generate the personal health record are described in U.S. patent application Ser. No. 10/159,489, entitled "Patient-Directed System and Method for Managing Medical Information" (hereinafter referred to as the Mok Patent Application"), filed May 31, 2002, which is incorporated by reference in its entirety for all purposes.

A medical record populator 205 is configured to populate preferred guideline 202 with displayed information. For example, information for treatment steps outlined in preferred guideline 202 may need to be inputted by the patient and/or by different medical providers 106 based on the treatment needs of the patient. The information may be automatically generated from medical records stored in a patient's personal health record. For example, the medical records for certain treatment steps may have been received from the patient and/or medical providers 106. If an x-ray had been performed, the x-ray results may have been received and stored in the patient's personal health record in data record PHR repository 108. This information may automatically be entered into preferred guideline 202 to indicate that an x-ray had been taken.

Also, a patient and other personal health record users may use interfaces to enter information into preferred guideline 202. For example, a physician may enter the date or timing of a treatment step to be performed into preferred guideline 202. Also, a patient may enter in the timing of the treatment step to be performed.

A score generator 206 is configured to measure the level of completeness (e.g., information adequacy score) of the medical records and other clinically-related information about the patient compiled in medical record populator 205. A score of 100% means that complete information is available in data record PHR repository 108 from which the patient and guideline users can make an informed decision about a particular treatment step. A score less than the acceptable threshold, for example 50%, means that more information or more medical records need to be collected, captured, or generated from medical providers 106. Alert generator 210 automatically generates an alert to recommend that certain tests or procedures be performed in order to generate the resulting information needed to make an informed decision about the next treatment step.

Score generator 206 is also configured to measure the degree of adherence (e.g., quality adherence score) to the recommended step(s) or successful completion of certain milestone(s) specified in the standard-of-care guideline. A score of 100% means that the patient and other users of the guideline are staying right on course with particular steps recommended by the guideline. A score less than the acceptable threshold, for example 50%, means that the patient and other users of the guideline need to follow the steps more closely or in a timelier manner. If a recommended step is missed or timeline for completion is delayed, alert generator 210 automatically generates an alert for certain steps be taken, taken sooner than planned, or taken before other steps.

A response monitor 208 is used to provide insert information into preferred guideline 202. For example, response monitor 208 receives input from a patient or medical providers 106 and inputs the information into preferred guideline 202.

Alert generator 210 is configured to generate alerts that notify the patient or medical providers 106 of missing information, missed treatment steps, or treatment steps that need to be taken earlier or sooner. For example, an alert may be sent to a patient when a threshold level of information adequacy or completeness has not been met. The patient may then authorize an alert to be sent to a medical provider 106 to request for the medical record information or to have certain procedures be performed in order to generate the needed information. For example, the alert may specify that a treatment step should be performed by a physician at a certain time. This reminds and communicates with users (physicians, patients, or other users) when decisions or actions have deviated from the standard of care guidelines. A check-and-balance framework promotes both physicians and patients to be in compliance with the standard of care guidelines. It also increases communication and collaboration between patients and physicians in evaluating treatment options and in taking actions that lead to better compliance. Patients can monitor whether they or their physicians are in compliance with quality guidelines and physicians can monitor whether they and their patients are in compliance with standard of care guidelines. Also, because standard of care guidelines are selected by a patient, the patient is aware of, has more information about, and can exercise more influence over the course of treatment steps being performed.

The following processes will now be described in more detail: generation of the patient preferred guidelines, assignment of users and requesting response from assigned users for the guide, alert generation, collection and categorization of medical records requested from medical providers 106, and retrieval of medical record information from personal health records in data record PHR repository 108.

Generation of Quality Adherence Guideline

Figure 3:
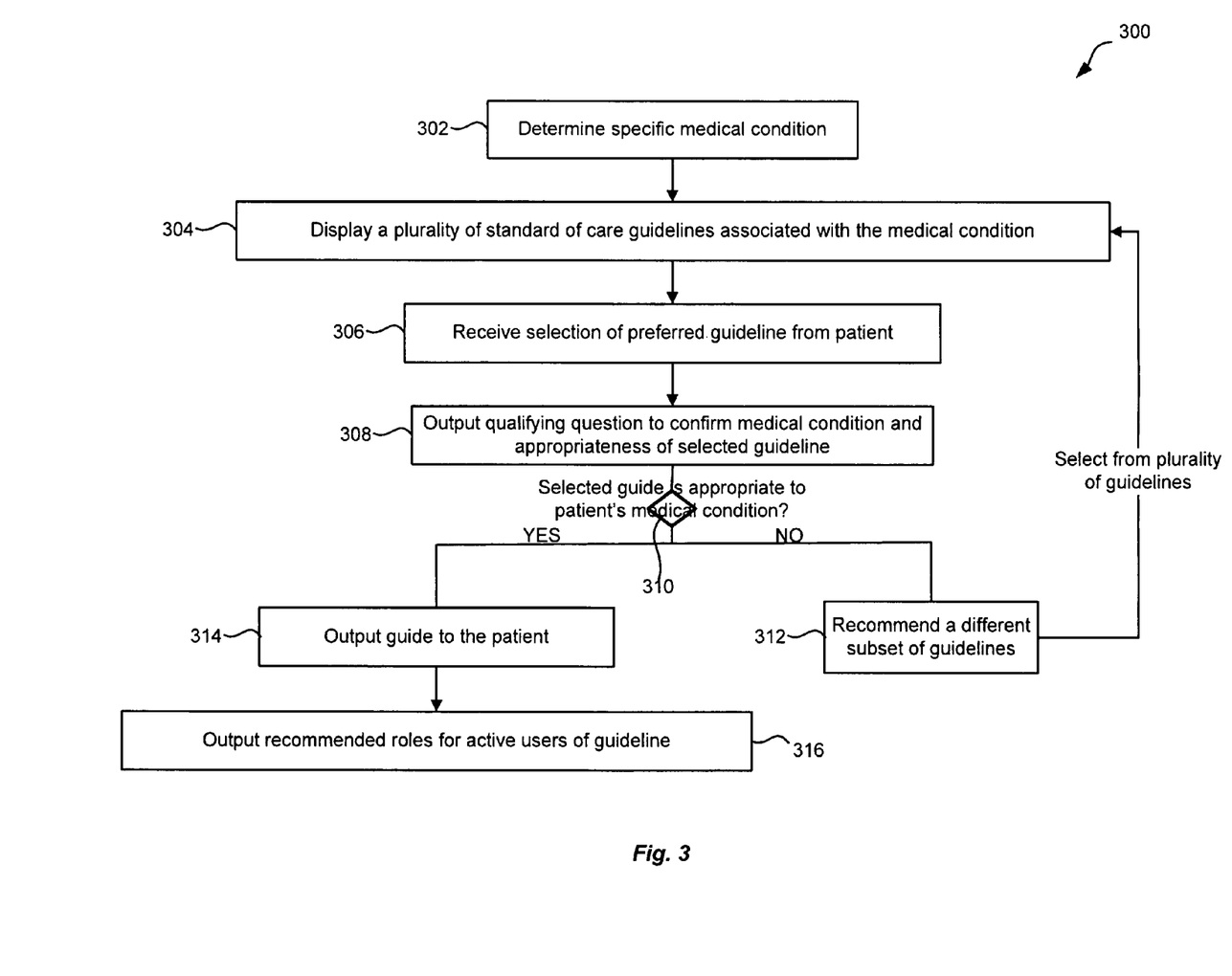
FIG. 3 depicts a simplified flowchart of a method for generating preferred quality adherence guideline according to one embodiment.

FIG. 3 depicts a simplified flowchart 300 of a method for generating preferred quality adherence guideline 202 according to one embodiment. Step 302 determines a specific medical condition for the patient. The medical condition may be a diagnosis for that medical condition the patient has received from medical provider 106. The diagnosis may be a specific disease type or condition type.

Step 304 displays a plurality of standard of care guidelines associated with the medical condition. For example, guideline generator 110 may search the plurality of standards of care guidelines 204 to determine which guidelines are associated with the medical condition. Different medical conditions may be associated with different treatment steps. A subgroup of standard of care guidelines may be determined and are output to the patient.

Step 306 receives a selection of a preferred guideline 202 from the patient. For example, the patient may review the standards of care guidelines and choose one that is desired. Also, in another embodiment, guideline generator 102 may automatically select a guideline that is considered to be the most relevant to the medical condition for the patient. In yet another embodiment, a user may select certain criteria or preferences that help narrow the displayed set of guidelines to a subset of those that match the criteria or preferences (e.g., a patient may prefer guidelines from a certain research institution).

In one embodiment, step 308 outputs one or more qualifying questions to confirm the medical condition and the appropriateness of the selected guide. For example, guideline generator 110 confirms that the medical condition that was input by the patient accurately describes the medical condition for the patient. In this example, guideline generator 110 may analyze information from the patient's personal health record to determine if the inputted medical condition by the user is appropriate. In another example, a guideline generator 110 asks questions as to whether the selected guideline is the guideline that is desired by the user. The outputted qualifying questions may describe the guideline and what treatment steps are covered by the guideline. The patient may then confirm that the guideline is appropriate.

Step 310 determines if the selected guideline is appropriate for the patient's medical condition. If the guideline is not, step 312 recommends a different subset of guidelines 204. For example, a patient may change the medical condition or further refine the medical condition, and a different set of guidelines 204 may be determined. The patient may then select one of these guidelines as the process reiterates to step 304.

If the selected guideline is appropriate, step 314 outputs the selected preferred guideline 202 to the patient. For example, preferred guideline 202 may be displayed on a user interface of client 104.

Figure 4:
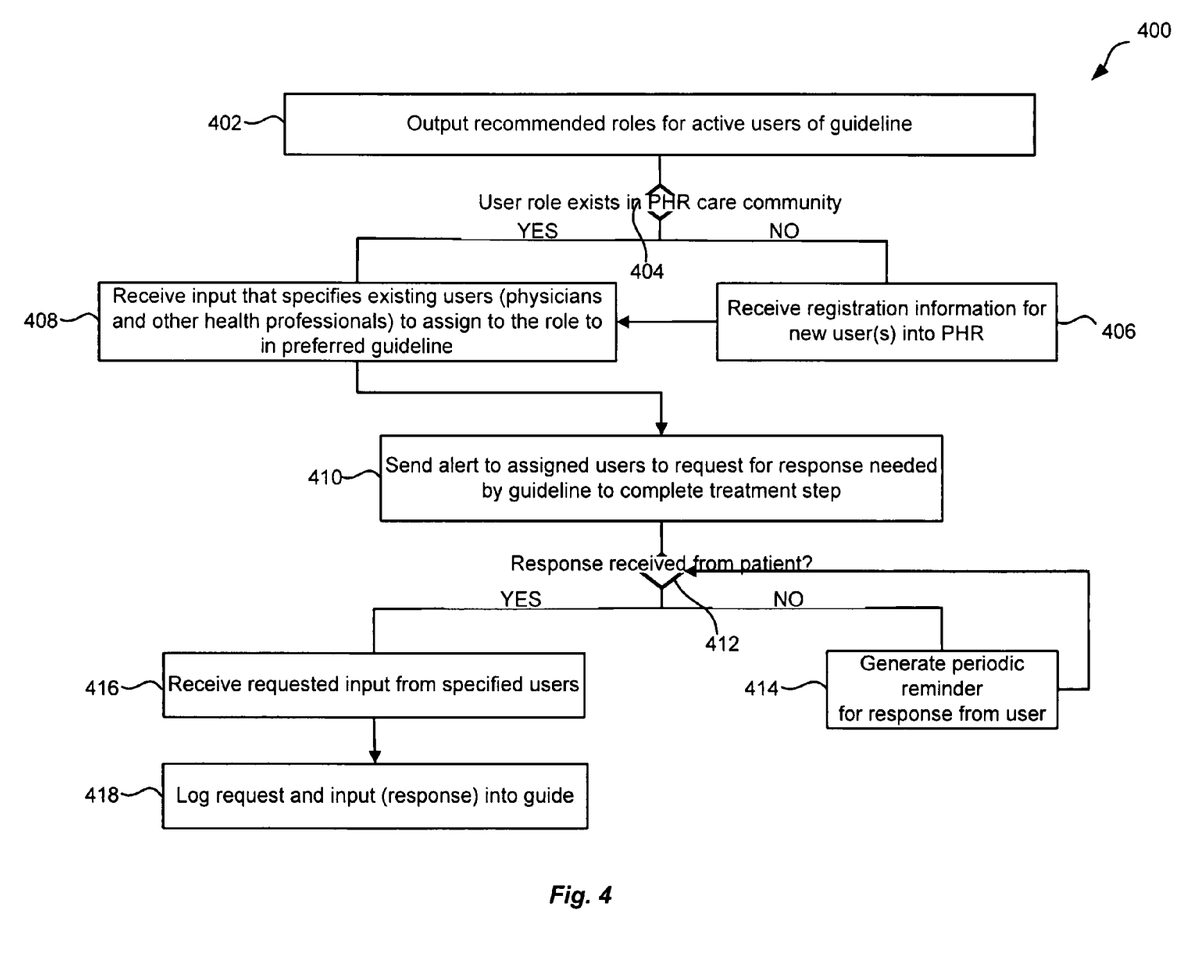
FIG. 4 depicts a simplified flowchart of a method for assigning user roles and requesting responses from certain type of assigned users according to one embodiment.

Step 316 outputs the recommended roles to participate as users of guideline 202. The recommended roles describe a type of user that should provide input for a treatment step in guideline 202. FIG. 4 describes the assignment of user roles.

Assignment of User Roles to Guideline

FIG. 4 depicts a simplified flowchart 400 of a method for assigning user roles and requesting responses from certain type of assigned users according to one embodiment. Guideline generator 110 may recommend certain roles to be assigned as respondents or participants of the guideline. This may include a description of the user type who should perform a treatment step in guideline 202 or respond to information requested about a treatment step as shown in FIG. 8, column 908, such as the role most suitable in answering the yes/no question about the recommended procedure or step. In one embodiment, a primary user is specified for completing the yes/no field and secondary users are also specified. The alert may be sent to the primary user and may also copy the secondary users. As shown, some roles include a breast surgeon, the patient, an oncologist, or any other physician.

Step 404 determines if a certain user role is taken or assigned to a unique user in the care community of the patient's personal health record. The patient may have a network of physicians in medical providers 106 that can provide the appropriate care. The role and its assigned users may already exist in this medical provider network. If a user role and user does not exist in the patient's care community, step 406 enables a patient to register or add a new user who can take on that role in the personal health record. For example, a patient may register new physicians or medical providers 106 into his/her personal health record system.

After registering a new user or if the user type already existed in the patient's care community, step 408 generates a list of qualifying users whose role matches that of the selected role specified in the guide 202 (e.g., physicians and other health professionals). The patient or other users then select the users from the list of qualifying users to be the active participants of guideline 202. There may be identifiers for specific users. For example, the role may have been breast surgeon and the identifier is a name of the physician selected to perform the surgery.

Guideline generator 110 then associates the assigned users to the roles in guideline 202. For example, contact information for the users may be stored and associated with each treatment step.

Step 410 sends a notification to the assigned PHR users to inform them of their participation in the guide 202 and to request a response (data input) that is needed by guideline 202 to complete the treatment step. The alerts may be sent at the appropriate defined times. In one example, a target date column 906 is used to determine when alerts should be sent as shown in FIG. 8. When a target date is reached or possibly before the target date, alert generator 210 determines an alert to send and also a user assigned to the role associated with the treatment step. The alert is generated and requests the user to provide information for the treatment step. As shown in column 906, the dates may be defined in different ways, such as within 2 weeks or a month of a biopsy; based on some medical criteria or results, such as if a tumor is less than 2 centimeters of the biopsy results; or other predetermined or hard-coded dates.

Step 412 determines if a response has been input by a user. If not, step 414 generates a periodic reminder for a response that is sent to the user assigned to the treatment step. The process reiterates to determine if the response has been received. If a response is received, step 416 receives the requested input from the specified users. Step 418 logs the response and also stores the input into the guide. The input may be stored automatically into the correct treatment step. For example, the user may download guideline 202 and directly enter the information into the guideline 202. Also, instead of entering information into guideline 202, a user may respond to an alert by sending a message (e.g., an email, letter) to user response monitor 208. User response monitor 208 may then determine the correct treatment step for which the input has been received and inputs this information automatically into guideline 202. For example, a treatment step identifier may be found on the medical record. Information for the treatment that was provided may be automatically inserted into preferred guideline 202, such as the date of the treatment.

Referring to FIG. 8, column 904 provides fields for input from users. In one example, a yes/no response may be required from the user role that has been assigned to column 908. This answers whether or not the procedure or decision step is planned or has been taken. If the answer is yes, a target date in column 906 is used to determine when the procedure or step has been taken. If the answer is no, then an alert may be generated about the missing procedure or decision step and used for determining the quality adherence score.

Column 906 is a target date. This may require a date from the assigned user to a timing of initiation of a procedure or decision step. If the date field is missing, guideline 202 may alert the appropriate user about the missing date. If the date field value falls outside of a recommended date (e.g., the date value is sooner or later than the calculated date based on a record number of days from previously-completed procedure or step), guideline 202 may alert the users to schedule or reschedule the procedure or decision step.

Alert Generation

Figure 5:
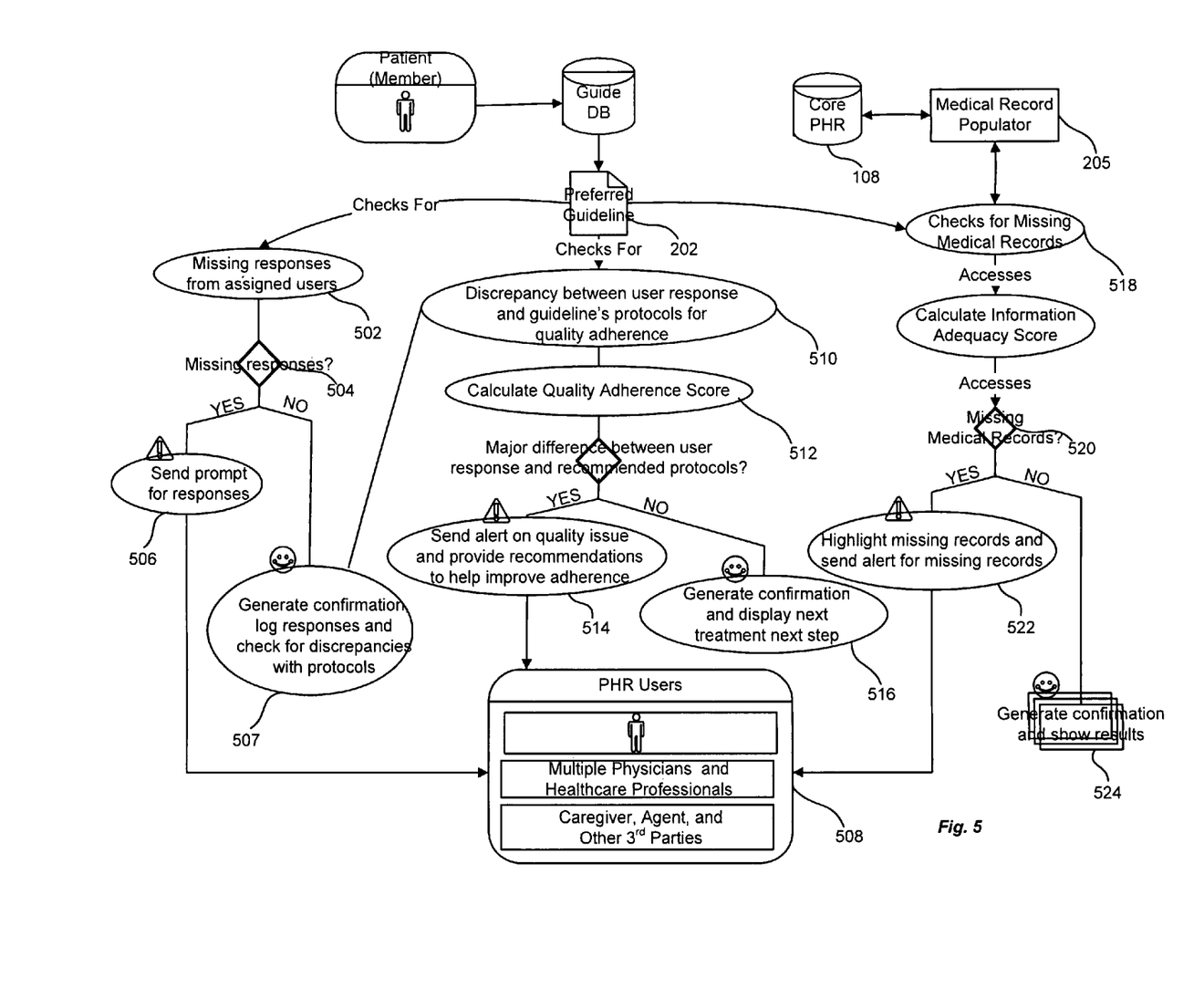
FIG. 5 depicts a simplified flow diagram for generating alerts according to one embodiment.

The alert generation as described above may include more detailed steps that may alert users for quality adherence issues. Preferred guideline 202 may automatically check for different issues associated with treatment steps. FIG. 5 depicts a simplified flow diagram 500 for generating alerts according to one embodiment. At step 502, guideline 202 checks for missing responses from assigned users. Step 504 determines if missing responses are found. If so, step 506 sends a prompt for a response to the assigned user. For example, guideline 202 determines which users are associated with the missing responses. Contact information can be determined and a prompt may be sent. As shown in 508, different PHR users may be contacted with alerts for responses. If missing responses are not found, in step 507, a confirmation is generated, and response are logged and reviewed for accuracy or discrepancies.

Guideline 202 may also assesses the information in the guideline for any discrepancies between the user response and guideline protocols for maintaining quality adherence in step 510.

Step 512 determines if there is a major difference between the user response and the guideline's best protocol. For example, different protocols may be provided for responses. In one example, if a date is required, the form of the date may be checked. Also, it is checked if the date is realistic. For example, a date that is entered in that is far in the future or in the past may not fall within the guideline's best protocol.

If there is a major difference, step 514 generates and sends an alert based on a quality issue and provides recommendations to help improve quality adherence. This recommendation may indicate the correct form that should be used for the input. The alert is sent to the assigned users in step 508.

If there is not a major difference, step 516 generates a confirmation and outputs recommendations of treatment next steps. For example, in FIG. 8, if a treatment step 902 has been completed, a recommendation for treatment step 910 may be generated and outputted. This may include sending an alert to the assigned user or notifying the patient of the next treatment step that is recommended.

Preferred guideline 202 may also check for missing medical records in step 518. In one example, medical providers 106 may download medical records to data record PHR repository 108 of a patient's personal health record. Guideline 202 may check whether medical records should be received for treatment steps. For example, treatment steps may be associated with a certain kind of medical record (a biopsy treatment step requires biopsy results). When a medical record is received for a patient's personal health record, it may be associated with a treatment step in guideline 202. If a record is not associated with a treatment step after a certain target date, it may be determined that a medical record is missing.

In step 520, it is determined if one of the ratings scores (e.g., information adequacy or quality adherence) is below a threshold. For example, a threshold may be a value for a quality adherence score or information adequacy score. Information adequacy may be below the threshold when a certain number of medical records may be missing. The medical records may be classified as critical or non-critical. For example, if a medical record is critical and missing, then an alert may be generated. However, certain non-critical medical records may not be necessary and guideline 202 may wait until a number of them are missing until an alert is generated. Also, non-critical medical records may not cause an alert to be generated until after a certain target date.

In step 522, if a ratings score is below a threshold, guideline 202 highlights steps to be taken to increase the rating score. For example, missing records are determined and alerts for the missing records are sent. Guideline 202 may determine the assigned users to the missing records and generates an alert for the users. The alert may then be sent to the user in step 508.

If a rating score is not below a threshold, in step 524, guideline 202 generates a confirmation and displays results. The results may be an information adequacy score or quality adherence score, both of which will be described below.

Collection and Categorization of Medical Records

Figure 6:
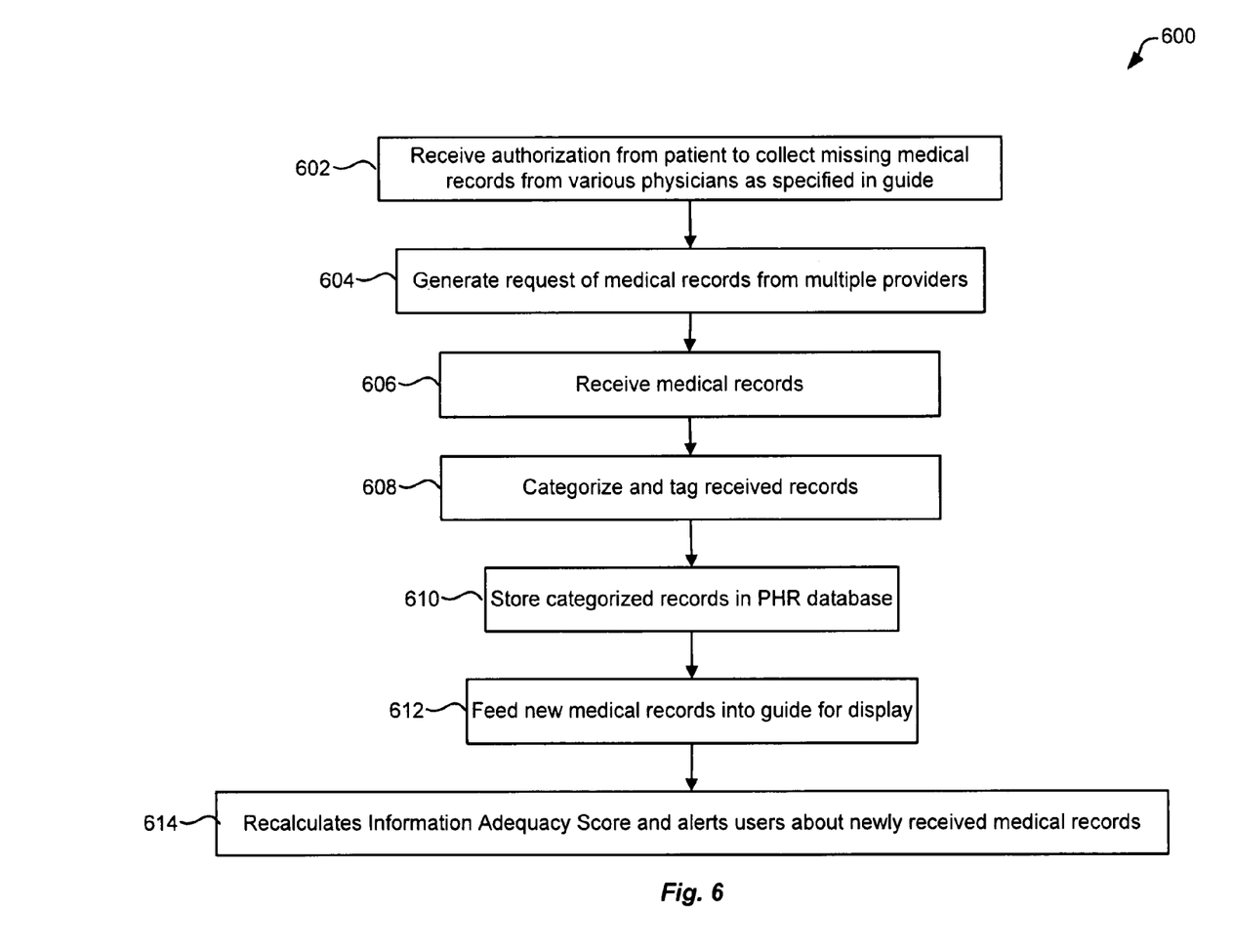
FIG. 6 depicts a simplified flowchart of a method for collecting and categorizing medical records requested from a plurality of medical providers according to one embodiment.

As discussed above with respect to step 522, alerts may be sent for missing medical records. The collection of missing medical records will now be described in more detail. FIG. 6 depicts a simplified flowchart 600 of a method for collecting and categorizing medical records requested from a plurality of medical providers 106 according to one embodiment. In step 602, guideline server 102 receives authorization from a patient to collect missing medical records from various medical providers 106 as specified in guideline 202. For example, guideline 202 may be analyzed to determine which medical records are missing from which physicians. The patient may be contacted and asked for permission to send alerts to the physicians for the missing medical records.

In step 604, guideline server 102 generates requests for medical records for the multiple medical providers 106. The requests may be associated with contact information for medical providers 106 that has been associated with guideline 202. The alerts may be sent through any methods, such as e-mail, regular mail, etc.

In step 606, medical records are received from medical providers 106. For example, the medical records may be in different forms, such as in soft copy, hard copy, or other media.

In step 608, the medical records are categorized and tagged. For example, guideline server 102 may categorize the medical records automatically. In one example, the categorization is performed based on who the medical record is received from. The medical records may be tagged according to whom it was received from, which treatment step it is associated with, a type of treatment, or with other categories. Also, users may also review the medical records and categorize and tag them. For example, if paper medical records are received, they may need to be scanned and categorized. Different methods of categorization are described in the Mok Patent Application.

In step 610, guideline server 102 stores the categorized records in database 108. The categorized records are stored and associated with the patient. For example, the medical records may be associated with the personal health record for the patient.

In step 612, information for the new medical records is inserted into guideline 202. For example, information for the medical records that is associated with treatment steps is inserted into guideline 202. In one example, if a medical provider 106 performed a biopsy, that medical record is determined and is associated with treatment step 902-2. A date is determined from the medical record and automatically inserted in the date field for the response column 904. Accordingly, guideline 202 is populated automatically based on the medical records received.

In step 614, guideline 202 calculates an information adequacy score and alerts users about newly-received medical records. For example, the additional information that is populated in guideline 202 may affect the information adequacy score. The calculation of the score will be described in more detail below.

Figure 7:
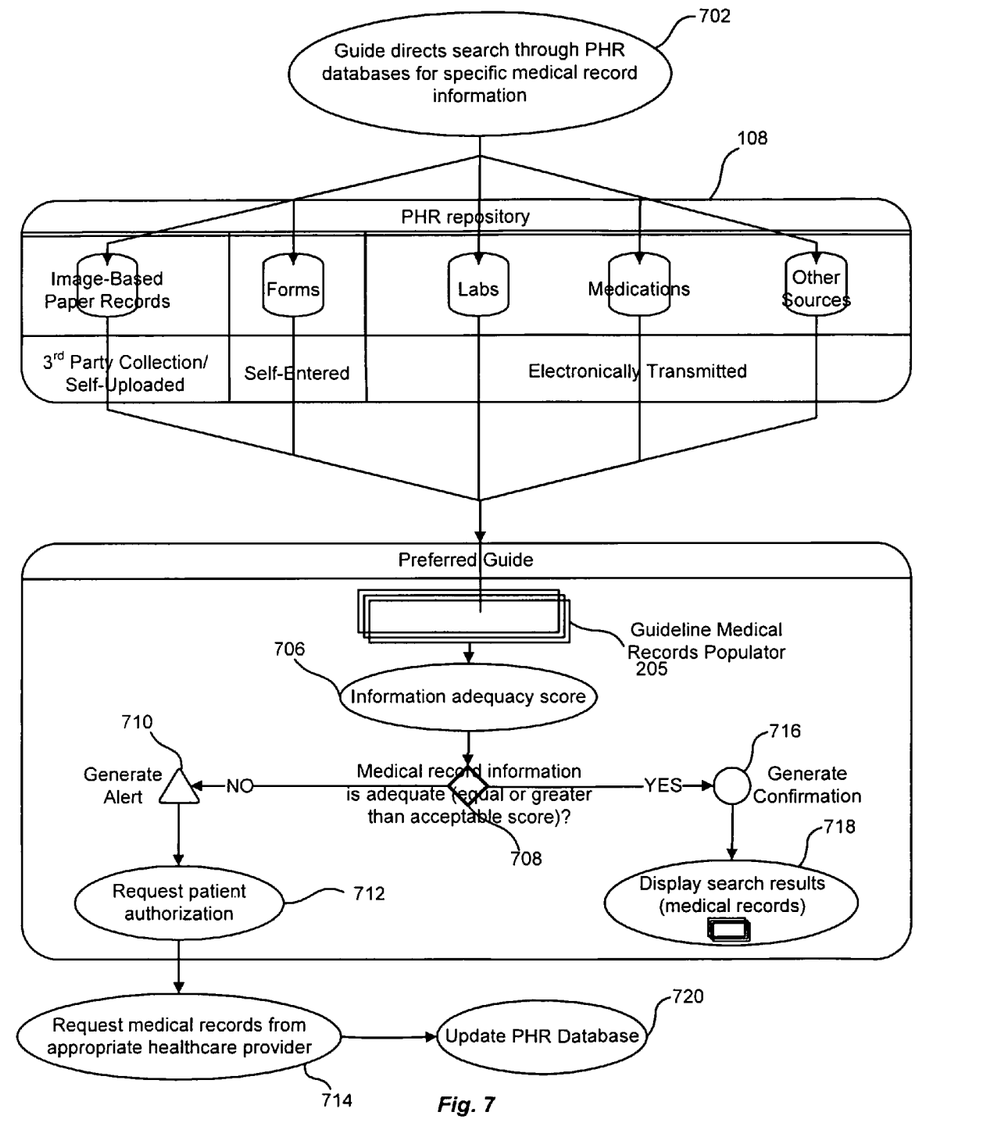
FIG. 7 shows a more detailed example of categorizing medical records according to one embodiment.

FIG. 7 shows a more detailed example of categorizing medical records according to one embodiment. At 702, guideline 202 is used to direct a search through personal health care database PHR repository 108 for specific medical record information. For example, a personal health record for a patient may include image-based paper records, guideline database, forms, lab results, medication information, or information from other sources. The results may be collected from a third-party collection service or self-uploaded, self-entered by the patient, or electronically transmitted.

The image-based paper records include paper records that have been scanned by a user. Also, the guideline database includes user input for different medical conditions as received from a patient or has been input by other users. Forms may be information that has been entered based on different forms, such as questionnaires. Lab results include lab results that have been electronically transmitted from medical providers 106. Medication information may be electronically transmitted from pharmacies.

These databases may be searched to determine which medical information is associated with guideline 202. The record information is input into guideline 202 and an information adequacy score 706 is determined. Information adequacy score may be shown on column 912 of guideline 202. As shown for treatment step 902, the information adequacy score is 45%.

Step 708 determines if medical record information is adequate. For example, a threshold for the information adequacy score may be used to determine if the medical record information is adequate. If the information adequacy score is not sufficient, an alert is generated at 710. At 712, patient authorization for sending the alert to an associated user may be requested. For example, a patient may direct who receives the alerts. In this case, guideline 202 determines which medical providers 106 are associated with the missing medical record information. The patient can then authorize whether or not the alert should be sent.

At step 714, medical records are collected from the appropriate medical providers 106. The databases can be updated as medical information is received from different from medical providers 106 at 720.

If the information adequacy score is adequate, at 716, a confirmation is generated. The results from the search may also be output in the form of guideline 202 at 718.

Information Adequacy Table

Figure 9:
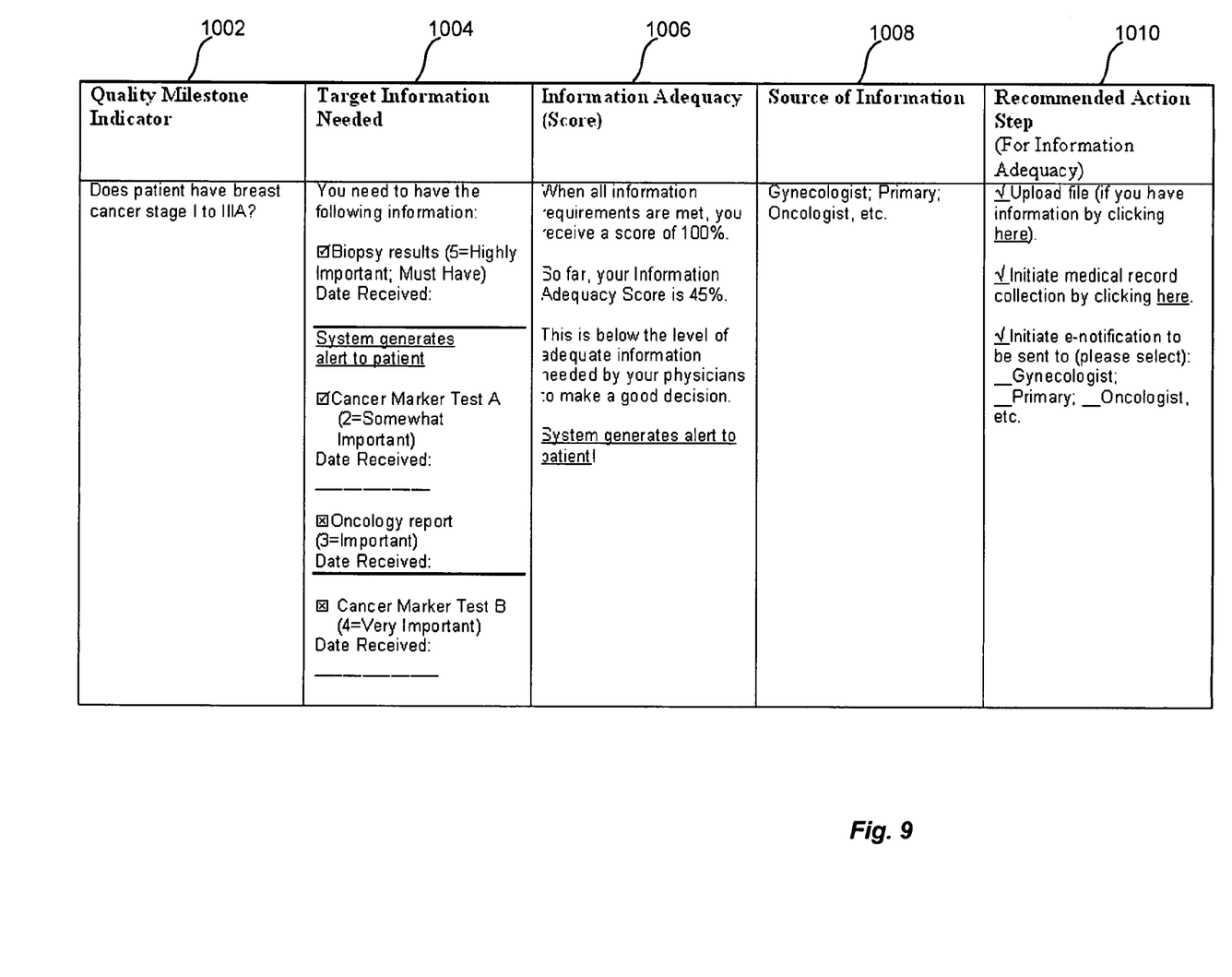
FIG. 9 shows an example of an information adequacy table according to one embodiment.

FIG. 9 shows an example of an information adequacy table 1000 according to one embodiment. As shown in table 1000, a Quality Milestone Indicator 1002 column shows the milestone that is being monitored. For this milestone, a Target Information Needed column 1004 indicates which information is needed. The information may include different tests or other results that can be garnered from medical records. Different target information is required, such as biopsy result, cancer marker test, and oncology report. An alert is generated if biopsy results are not received by a certain date.

An Information Adequacy Score column 1006 shows the information adequacy score. For example, depending on the amount of information that has been received, the score is generated. Column 1006 may also indicate that the score is below a desired level in which case alerts may also be generated here.

A Source of Information column 1008 indicates the sources of information from which medical records have been received. The sources may be from medical providers 106 or the patient.

A Recommended Action step column 1010 indicates actions that need to be taken. For example, based on the medical information received, different actions should be taken to increase the information adequacy score. As these steps are taken, the information adequacy score may be increased.

The information adequacy score provides a way for patients and physicians to know whether they have had adequate information from which to make decisions about a recommended course of care. An information adequacy score provides a measure of how much information is missing. This provides a way for patients and physicians to know when new information has been captured into guideline 202. Guideline 202 then allows patients to request from their physicians certain procedures or treatment steps as specified in guideline 202. This may increase the information adequacy score as these steps or milestones are taken. Also, it allows the patient to request collection of medical information when it is determined that information is missing for the steps.

The information adequacy score may be weighted based on the availability and importance of each type of information. A weighted average may be calculated between yes (100%) or no (0%) values that are attributed to various levels of importance (e.g., extremely important (5), very important (4), important (3), somewhat important (2), not important (1)). For example, scales can be applied to score various lab test results that can help physicians evaluate the feasibility of the next treatment step. As shown, Biopsy results, Oncology report, and Cancer Marker test are rated as Must Have and are worth 4 points. The Mammogram is rated at 1, not important or relevant, since the patient is presumably at post-diagnosis stage and has already received the results of the biopsy. For example, if the Biopsy results are missing, the quality adherence score would be lower than if the Mammogram is missing. Also, the score would be higher if the Biopsy results are eventually performed versus whether a Mammogram is received. The total score based on the yes or no values is compared to the ideal when each piece of information is available in the guide.

Based on the information provided, an information adequacy score is then generated. The score shows the user how complete the medical record history is for the user. Thus, the user may quickly determine how medical providers 106 have been providing treatment. This may depend on which medical information has been entered into guideline 202, which indicates whether the appropriate steps have been taken. If the user is receiving a low score, then the patient may want to check to see what treatment steps need to be taken and when. The score is a quick way for a patient to access the treatment being received from multiple medical providers 106.

The quality adherence score is calculated in the same way as information adequacy except that the score measures the closeness (proximity) of the actual action or timing of the action with the guideline recommended action. The weighted average number is produced when the value representing the status of the action (yes, no, or somewhat taken) is weighted by the value representing the importance of each guideline step.

Advantages

Particular embodiments provide many advantages. For example, particular embodiments increase the participation and the role of patients in monitoring the quality of care, decision making process, and recommended actions. This may lead to a better health outcome for the patient. Delays (elapsed time) between diagnosis and first treatment step are reduced because treatment steps are provided to a user.

The collaboration between patient and physician for achieving quality guideline goals is enhanced because of the communication the guide provides. Particular embodiments also provide an equal level of invested interest and ownership in quality performance measures (based on industry-approved quality of care guidelines) and patient's health outcome. Patient knowledge about treatment choices and next steps in process is also increased due to the treatment steps generated for the guide. The guide also improves overall adherence to quality of care and coordination of information flow.

The quality of care and information flow is also measured using the quality adherence score and information adequacy score. Physician time and effort is saved by enabling them to know whether they have adequate and right information when making decisions about care.

There are positive implications for research and regulatory purposes that require assessment of adherence to care guidelines by specific sub-segment of the patient population. Also, there are positive implications for improving the quality of individual patient care as well retrospective examination of physician performance according to the standards of care as defined by university-based or industry-approved guidelines.

Although the description has been described with respect to particular embodiments thereof, these particular embodiments are merely illustrative, and not restrictive. Any suitable programming language can be used to implement the routines of particular embodiments including C, C++, Java, assembly language, etc. Different programming techniques can be employed such as procedural or object oriented. The routines can execute on a single processing device or multiple processors. Although the steps, operations, or computations may be presented in a specific order, this order may be changed in different particular embodiments. In some particular embodiments, multiple steps shown as sequential in this specification can be performed at the same time.

Particular embodiments may be implemented in a computer-readable storage medium for use by or in connection with the instruction execution system, apparatus, system, or device. Particular embodiments can be implemented in the form of control logic in software or hardware or a combination of both. The control logic, when executed by one or more processors, may be operable to perform that which is described in particular embodiments.

Particular embodiments may be implemented by using a programmed general purpose digital computer, by using application specific integrated circuits, programmable logic devices, field programmable gate arrays, optical, chemical, biological, quantum or nanoengineered systems, components and mechanisms may be used. In general, the functions of particular embodiments can be achieved by any means as is known in the art. Distributed, networked systems, components, and/or circuits can be used. Communication, or transfer, of data may be wired, wireless, or by any other means.

It will also be appreciated that one or more of the elements depicted in the drawings/figures can also be implemented in a more separated or integrated manner, or even removed or rendered as inoperable in certain cases, as is useful in accordance with a particular application. It is also within the spirit and scope to implement a program or code that can be stored in a machine-readable medium to permit a computer to perform any of the methods described above.

As used in the description herein and throughout the claims that follow, "a", "an", and "the" includes plural references unless the context clearly dictates otherwise. Also, as used in the description herein and throughout the claims that follow, the meaning of "in" includes "in" and "on" unless the context clearly dictates otherwise.

Thus, while particular embodiments have been described herein, latitudes of modification, various changes, and substitutions are intended in the foregoing disclosures, and it will be appreciated that in some instances some features of particular embodiments will be employed without a corresponding use of other features without departing from the scope and spirit as set forth. Therefore, many modifications may be made to adapt a particular situation or material to the essential scope and spirit.

We claim:

1. A method for using a quality adherence guideline for a patient, the method comprising:
   receiving, by a computing device, a plurality of medical records from a plurality of medical providers, the patient authorizing release of the plurality of medical records from the plurality of medical providers affiliated with different organizations, each medical provider owning a subset of medical records in the plurality of medical records for the user;
   classifying medical records in the plurality of medical records with classification tags based on a category determined to be associated with each medical record and storing the classified medical records in a database;
   receiving an input for a standard of care from a plurality of standards of care, the standards of care related to a medical condition associated with the patient and including different sets of treatment steps of recommended medical solutions;
   generating, by the computing device, a quality adherence guideline using the selected standard of care and information from the plurality of medical records received from the plurality of medical providers, the quality adherence guideline including a set of treatment steps defined by the selected standard of care related to the medical condition, wherein information from the plurality of medical records stored in the database is automatically inserted into the guideline and associated with the set of treatment steps based on classification tags associated with the plurality of medical records that are used to match medical records to treatment steps;
   assigning a plurality of users from two or more of the plurality of medical providers to one or more treatment steps in the set of treatment steps based on input by the patient;
   receiving input from the plurality of users regarding one or more treatment steps in the set of treatment steps, the input from the plurality of users related to the patient's treatment with regard to the one or more treatment steps;
   analyzing, by the computing device, the quality adherence guideline to determine if the standard of care is being adhered to based on the received input from the plurality of users and based on the information from the plurality of medical records received from the plurality of medical providers, wherein analyzing comprises determining a quality adherence score based on analysis of at least a portion of the input from the plurality of users, at least a portion of the information from the plurality of medical records, and at least a portion of recommended steps specified in the quality adherence guide, the quality adherence score rating indicating whether the standard of care is being adhered to; and
   outputting an alert based on the analysis regarding quality adherence to the standard of care.

2. The method of claim 1, wherein the plurality of medical providers are affiliated with different organizations that create documentation about the patient using different formats or medium of documentation.

3. The method of claim 1, wherein the plurality of standards of care include a standard of care not developed or previously used by one of the plurality of medical providers.

4. The method of claim 3, wherein receiving the input for the standard of care comprises receiving the input from the patient or one of the plurality of medical providers selecting the standard of care.

5. The method of claim 1, further comprising receiving input regarding a diagnosis of a disease or medical condition in order to generate the plurality of standards of care related to the medical condition associated with the patient.

6. The method of claim 1, further comprising receiving input from the patient regarding information for a treatment step in the set of treatment steps.

7. The method of claim 1, wherein generating the alert comprises generating a message based on analyzing the information inputted and the information from a plurality of medical records inserted into the quality adherence guide, the alert reminding the patient that a target of a treatment step has not been achieved based on the time considered due.

8. The method of claim 1, wherein the two or more users comprise two or more physicians treating the patient.

9. The method of claim 1, further comprising sending a message to each of the two or more users indicating input is needed for the associated steps for the patient.

10. The method of claim 1, wherein a treatment step in the quality adherence guideline comprises a response field, target date field, and assignment to a user associated with a medical provider, the response field indicating a response is needed from the user and the target date indicating a by which that the response is needed.

11. The method of claim 1, wherein the treatment step includes a field showing a plurality of information needed from a plurality of medical providers in order to evaluate appropriateness of the treatment step.

12. The method of claim 11, wherein the field includes an information adequacy score measuring the amount and importance of information that has been received for the step based on an amount and importance of information that is needed from the plurality of medical providers for the information adequacy to be considered complete for evaluating appropriateness of the treatment step.

13. The method of claim 12, wherein the field includes a recommended next action treatment step indicating an action the patient or assigned one or more users should perform based on the information received for the treatment step.

14. The method of claim 1, wherein the plurality of standards of care are generated by medical research institutions.

15. The method of claim 1, further comprising receiving input from the patient assigning specific users to receive alerts to input information into the quality adherence guide.

16. The method of claim 1, wherein:
   a treatment step is associated with a threshold, wherein analyzing comprises determining if received input for the treatment step exceeds the threshold, and outputting the alert when the threshold is exceeded.

17. An apparatus configured to use a quality adherence guideline for a patient, the apparatus comprising:
one or more computer processors; and
logic encoded in one or more tangible storage media for execution by the one or more computer processors and when executed operable to:
receive a plurality of medical records from a plurality of medical providers, the patient authorizing release of the plurality of medical records from the plurality of medical providers affiliated with different organizations, each medical provider owning a subset of medical records in the plurality of medical records for the user;
classify medical records in the plurality of medical records with classification tags based on a category determined to be associated with each medical record and storing the classified medical records in a database;
receive an input for a standard of care from a plurality of standards of care, the standards of care related to a medical condition associated with the patient and including different sets of treatment steps of recommended medical solutions;
generate a quality adherence guideline using the selected standard of care and information from the plurality of medical records received from the plurality of medical providers, the quality adherence guideline including a set of treatment steps defined by the selected standard of care related to the medical condition, wherein information from the plurality of medical records stored in the database is automatically inserted into the guideline and associated with the set of treatment steps based on classification tags associated with the plurality of medical records that are used to match medical records to treatment steps;
assign a plurality of users from two or more of the plurality of medical providers to one or more treatment steps in the set of treatment steps based on input by the patient;
receive input from the plurality of users regarding one or more treatment steps in the set of treatment steps, the input from the plurality of users related to the patient's treatment with regard to the one or more treatment steps;
analyze the quality adherence guideline to determine if the standard of care is being adhered to based on the received input from the plurality of users and based on the information from the plurality of medical records received from the plurality of medical providers, wherein analyze comprises determine a quality adherence score based on analysis of at least a portion of the input from the plurality of users, at least a portion of the information from the plurality of medical records, and at least a portion of recommended steps specified in the quality adherence guide, the quality adherence score rating indicating whether the standard of care is being adhered to; and
output an alert based on the analysis regarding quality adherence to the standard of care.

18. The apparatus of claim 17, wherein the treatment step includes a field showing a plurality of information needed from a plurality of medical providers in order to evaluate appropriateness of the treatment step.

19. The apparatus of claim 18, wherein the field includes an information adequacy score measuring the amount and importance of information that has been received for the step based on an amount and importance of information that is needed from the plurality of medical providers for the information adequacy to be considered complete for evaluating appropriateness of the step.

20. A system for using a quality adherence guideline for a patient, the system comprising:
means for receiving a plurality of medical records from a plurality of medical providers, the patient authorizing release of the plurality of medical records from the plurality of medical providers affiliated with different organizations, each medical provider owning a subset of medical records in the plurality of medical records for the user;
means for classifying medical records in the plurality of medical records with classification tags based on a category determined to be associated with each medical record and storing the classified medical records in a database;
means for receiving an input for a standard of care from a plurality of standards of care, the standards of care related to a medical condition associated with the patient and including different sets of treatment steps of recommended medical solutions;
means for generating a quality adherence guideline using the selected standard of care and information from the plurality of medical records received from the plurality of medical providers, the quality adherence guideline including a set of treatment steps defined by the selected standard of care related to the medical condition, wherein information from the plurality of medical records stored in the database is automatically inserted into the guideline and associated with the set of treatment steps based on classification tags associated with the plurality of medical records that are used to match medical records to treatment steps;
means for assigning a plurality of users from two or more of the plurality of medical providers to one or more treatment steps in the set of treatment steps based on input by the patient;
means for receiving input from the plurality of users regarding one or more treatment steps in the set of treatment steps, the input from the plurality of users related to the patient's treatment with regard to the one or more treatment steps;
means for analyzing the quality adherence guideline to determine if the standard of care is being adhered to based on the received input from the plurality of users and based on the information from the plurality of medical records received from the plurality of medical providers, wherein analyzing comprises determining a quality adherence score based on analysis of at least a portion of the input from the plurality of users, at least a portion of the information from the plurality of medical records, and at least a portion of recommended steps specified in the quality adherence guide, the quality adherence score rating indicating whether the standard of care is being adhered to; and
means for outputting an alert based on the analysis regarding quality adherence to the standard of care.

* * * * *